(12) United States Patent
Suh et al.

(10) Patent No.: US 10,064,597 B2
(45) Date of Patent: Sep. 4, 2018

(54) HEAD AND NECK SIMULATION PHANTOM DEVICE

(71) Applicant: CATHOLIC UNIVERSITY INDUSTRY-ACADEMIC COOPERATION FOUNDATION, Seoul (KR)

(72) Inventors: Tae Suk Suh, Seoul (KR); Min Young Lee, Seoul (KR); Ji Yeon Park, Seoul (KR); Jeong Woo Lee, Seoul (KR); Joon Yong Choi, Gyeonggi-do (KR); Sang Won Kang, Seoul (KR); Hae Jin Park, Gyeonggi-do (KR)

(73) Assignee: The Catholic University of Korea Industry—Academic Cooperation Foundation, Seoul (KR)

( * ) Notice: Subject to any disclaimer, the term of this patent is extended or adjusted under 35 U.S.C. 154(b) by 76 days.

(21) Appl. No.: 15/101,071

(22) PCT Filed: Apr. 2, 2015

(86) PCT No.: PCT/KR2015/003331
§ 371 (c)(1),
(2) Date: Jun. 2, 2016

(87) PCT Pub. No.: WO2016/137053
PCT Pub. Date: Sep. 1, 2016

(65) Prior Publication Data
US 2017/0000452 A1    Jan. 5, 2017

(30) Foreign Application Priority Data
Feb. 24, 2015 (KR) .......................... 10-2015-0025627

(51) Int. Cl.
*A61B 6/00* (2006.01)
*A61B 6/14* (2006.01)
(Continued)

(52) U.S. Cl.
CPC .............. *A61B 6/583* (2013.01); *A61B 6/032* (2013.01); *A61B 6/14* (2013.01); *A61B 6/542* (2013.01);
(Continued)

(58) Field of Classification Search
CPC ........... A61B 6/583; A61B 6/032; A61B 6/14; A61B 6/542; G01T 1/06; G01T 1/11
See application file for complete search history.

(56) References Cited

U.S. PATENT DOCUMENTS 7,728,285 B2 * 6/2010 Suh ...................... A61N 5/1048
                                                                    250/252.1
8,708,562 B1 * 4/2014 Nosil .................... A61B 6/583
                                                                    378/207

(Continued)

OTHER PUBLICATIONS

Wu et al., Radiation dose evaluation of dental cone beam computed tomography using an anthropomorphic adult head phantom,Dec. 4, 2014, Radiation Physics and Chemistry, Vo. 104, pp. 287-291.*

*Primary Examiner* — Christine Sung
(74) *Attorney, Agent, or Firm* — Eric W. Cernyar; James W. Huffman

(57) ABSTRACT

The present invention relates to a head and neck simulation phantom device for simulating the head and neck of a body, the phantom device including: a flat type first plate having a first insertion groove formed on one surface thereof; a flat type second plate disposed to come into contact with the other surface of the first plate and having a second insertion groove formed on the contacted surface with the other surface of the first plate in such a manner as to correspond to the first insertion groove; and a plurality of teeth simulants inserted into the first insertion groove and the second insertion groove and for simulating the teeth of the body.

12 Claims, 7 Drawing Sheets

(51) Int. Cl.
*A61B 6/03* (2006.01)
*G01T 1/169* (2006.01)
*G01T 1/06* (2006.01)
*G01T 1/11* (2006.01)

(52) U.S. Cl.
CPC ............... *G01T 1/169* (2013.01); *G01T 1/06* (2013.01); *G01T 1/11* (2013.01)

(56) References Cited

U.S. PATENT DOCUMENTS

| | | | |
|---|---|---|---|
| 9,625,584 B1* | 4/2017 | Cox | G01T 1/1648 |
| 2010/0074414 A1* | 3/2010 | Katsuda | A61B 6/583 |
| | | | 378/207 |
| 2011/0096911 A1* | 4/2011 | Dove | A61B 6/145 |
| | | | 378/207 |
| 2012/0201438 A1* | 8/2012 | Vermandel | G01N 29/0654 |
| | | | 382/128 |
| 2013/0114799 A1* | 5/2013 | Yamakawa | A61B 6/14 |
| | | | 378/207 |

* cited by examiner

HEAD AND NECK SIMULATION PHANTOM DEVICE

BACKGROUND OF THE INVENTION

Field of the Invention

The present invention relates to a head and neck simulation phantom device, and more particularly, to a head and neck simulation phantom device that is capable of measuring radiation, instead of the human body, and evaluating dose errors generated from teeth and implants within the body.

The present invention further relates to a head and neck simulation phantom device and that is capable of selectively disposing teeth and implants to express the real state of a patient's teeth, so that artifacts appearing on computed tomography CT images by the teeth and implants are obtained, thereby conducting dose verification on the corresponding regions of the CT images at which the artifacts appear.

Background of the Related Art

Head and neck cancers contain various kinds of cancers such as laryngeal cancer, oral cancer, nasal cavity cancer, pharyngeal cancer and so on, and since their ranges for treatment are relatively large and their shapes are irregular, radiation treatment is frequently and usefully applied to them. According to the biological characteristics of the head and neck cancers and the development of radiation treatment technologies, clinical treatment effects are gradually increased, and the exposure dose to salivary glands and eyeballs as main protection organs becomes minimized, thereby making it possible to conduct radiation treatment more accurately and effectively.

So as to predict the absorbed dose to the patient upon the radiation treatment of his or her head and neck cancer, CT images are photographed before the radiation treatment, and the absorbed dose is predicted from the CT images by using information (for example, Hounsfield Unit HU and electron density), and after the predicted absorbed dose is optimized, the radiation treatment starts. Accordingly, the qualities of CT images should be excellent because the cancer to which the dose is transmitted and the protection organs on which the transmitted dose has to be minimized are defined more accurately on the basis of the CT images, and further, the electron density of the treatment region is obtained from the CT images, thereby conducting the dose calculation more accurately. So as to conduct the radiation treatment more accurately and safely, above all, it is very important to acquire the CT images having excellent qualities and accurate information.

By the way, if the CT photographing for the head and neck cancer patient is conducted for his or her radiation treatment in the state where he or she wears dental prosthesis like implants, higher atomic number materials than HU 2000, like titanium used as the materials of the implants, are contained in the reconstruction of the CT images, so that they appear on the CT images, as artifacts which do not exist really around the implants but look like they exist on the CT images. Therefore, different values from the inherent HU values of the real treatment region are expressed on the CT images. Such artifacts appearing on the CT images cause the qualities of images to be deteriorated, and further, the information required for dose calculation is not accurately obtained from the CT images, thereby increasing predicted dose errors.

So as to enhance the accuracy in prediction of the dose on the CT images upon radiation treatment planning, accordingly, the CT images on which the artifacts are corrected are required. As a result, algorithms for restoring or correcting the image information damaged by the artifacts have been applied in a variety of ways, and further, many studies on the reconstruction of CT images with improved quality have been proposed wherein the CT photographing is used together with megavoltage CT or PET on which artifacts generated from high atomic number metal materials are relatively small. However, even if the qualities of gross and quantitative images are improved through the post process on the images, it should be verified whether how much the dose prediction is accurate so as to trust the image information restored from the points at which the artifacts are produced. Accordingly, the accurate prediction in the quantity of absorbed dose to be transmitted to the patient is more specified and quantified, and through the accurate prediction, there is a need to select effective artifact reducing algorithm.

Generally, the head and neck are representative regions on which artifacts are typically produced upon the reconstruction of CT images due to the use of the patient's dental prosthesis like implants. Further, the component ratios of non-uniform materials like mouth and mandible are high so that there is a high probability of the generation of dose errors. Therefore, there is a need for evaluating the accuracy in the prediction of the absorbed dose of the teeth and implants on the CT images upon the radiation treatment, while the teeth and implants are simulating the patient's head and neck region and mouth structure and the dose verification for them is being conducted. Further, there is a need for a head and neck simulation phantom device that is capable of selectively disposing the teeth and implants to express the real state of the patient's teeth, so that artifacts appearing on the CT images by the teeth and implants are accurately obtained, thereby conducting dose verification on the corresponding regions of the CT images at which the artifacts appear.

SUMMARY OF THE INVENTION

Accordingly, the present invention has been made in view of the above-mentioned problems occurring in the prior art, and it is an object of the present invention to provide a head and neck simulation phantom device that is capable of measuring radiation, instead of the human body, and evaluating dose errors generated from teeth and implants within the body.

It is another object of the present invention to provide a head and neck simulation phantom device that is capable of selectively disposing teeth and implants to express the real state of a patient's teeth, so that artifacts appearing on computed tomography CT images by the teeth and implants are obtained, thereby conducting dose verification on the corresponding regions of the CT images at which the artifacts appear.

To accomplish the above-mentioned objects, according to the present invention, there is provided a head and neck simulation phantom device for simulating the head and neck of a body, the phantom device including: a flat type first plate having a first insertion groove formed on one surface thereof; a flat type second plate disposed to come into contact with the other surface of the first plate and having a second insertion groove formed on the contacted surface with the other surface of the first plate in such a manner as to correspond to the first insertion groove; and a plurality of teeth simulants inserted into the first insertion groove and the second insertion groove and for simulating the teeth of the body.

According to the present invention, desirably, the first plate and the second plate have through holes formed penetratedly thereinto.

According to the present invention, desirably, each teeth simulant includes: a cylindrical case; and an accommodated material located in the case.

According to the present invention, desirably, the accommodated material includes a titanium material.

According to the present invention, desirably, the case is made of a thermoplastic material.

According to the present invention, desirably, the first plate and the second plate have dosimeter insertion grooves formed along the outer edges of the first insertion groove and the second insertion groove in such a manner as to penetrate into the contacted surface therebetween and to insert dosimeters for radiation measurement thereinto.

According to the present invention, desirably, the dosimeters are inserted into the first plate and the second plate by half of the length.

According to the present invention, desirably, the first plate and the second plate have a film therebetween so as to measure radiation dose distribution.

According to the present invention, desirably, the head and neck simulation phantom device further includes couplers inserted penetratedly into fastening holes formed penetratedly into the first plate and the second plate so as to couple the first plate and the second plate to each other.

According to the present invention, desirably, the head and neck simulation phantom device further includes at least one or more intermediate plates disposed between the first plate and the second plate and having an opening formed thereon in such a manner as to correspond to the first insertion groove and the second insertion groove.

According to the present invention, desirably, the first plate, the second plate and the intermediate plate have dosimeter insertion grooves formed along the outer edges of the first insertion groove and the second insertion groove in such a manner as to penetrate into the contacted surface between the first plate and the intermediate plate and the contacted surface between the second plate and the intermediate plate and to insert dosimeters for radiation measurement thereinto.

According to the present invention, desirably, the dosimeters are inserted into the first plate and the intermediate plate by half of the length and into the second plate and the intermediate plate by half of the length.

According to the present invention, desirably, the first plate and the intermediate plate have a film disposed therebetween and the intermediate plate and the second plate have a film disposed therebetween, so as to measure radiation dose distribution.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Figure 1:
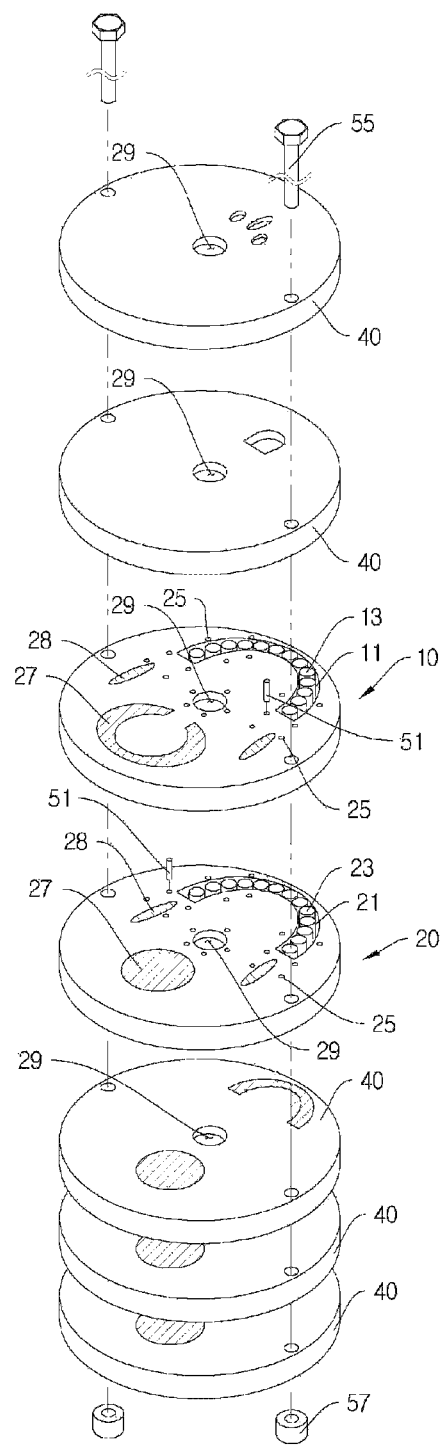
FIG. 1 is an exploded perspective view showing a head and neck simulation phantom device according to a first embodiment of the present invention.

The present invention may be modified in various ways and may have several exemplary embodiments. Specific exemplary embodiments of the present invention are illustrated in the drawings and described in detail in the detailed description. However, this does not limit the invention within specific embodiments and it should be understood that the invention covers all the modifications, equivalents, and replacements within the idea and technical scope of the invention. If it is determined that the detailed explanation on the well known technology related to the present invention makes the scope of the present invention not clear, the explanation will be avoided for the brevity of the description.

Terms, such as the first and the second may be used to describe various elements, but the elements should not be restricted by the terms. The terms are used to only distinguish one element from the other element.

Hereinafter, an explanation on a head and neck simulation phantom device according to the present invention will be in detail given with reference to the attached drawing. The present invention is disclosed with reference to the attached drawings wherein the corresponding parts in the embodiments of the present invention are indicated by corresponding reference numerals and the repeated explanation on the corresponding parts will be avoided.

Figure 5:
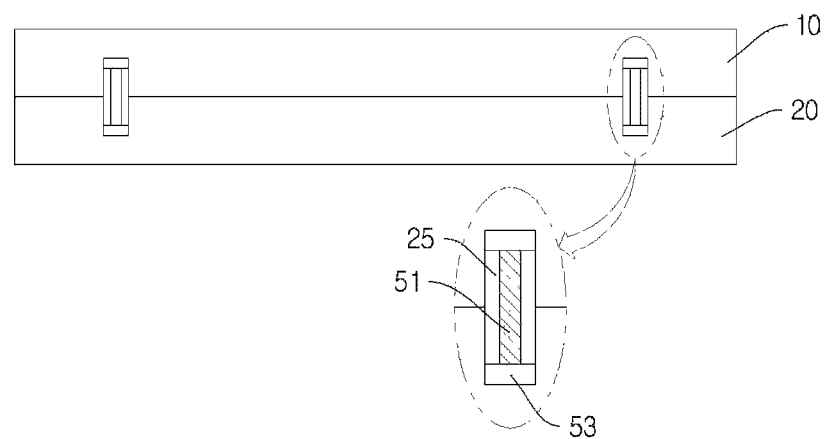
Figure 6:
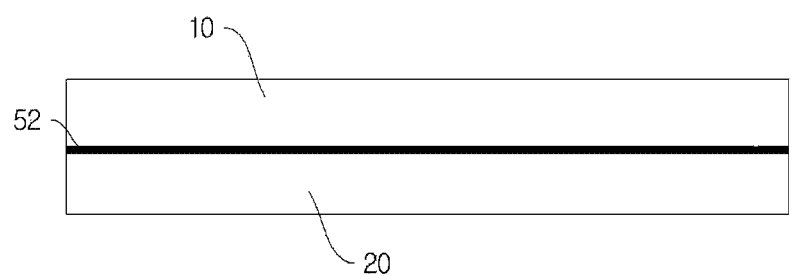
Figure 7:
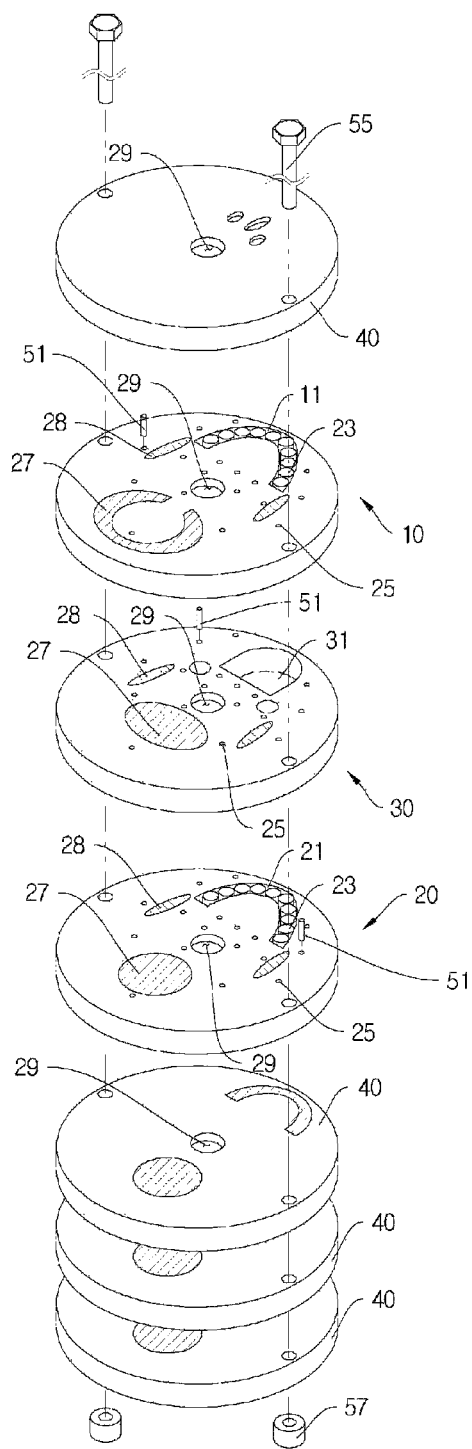
FIG. 7 is an exploded perspective view showing a head and neck simulation phantom device according to a second embodiment of the present invention.
Figure 8:
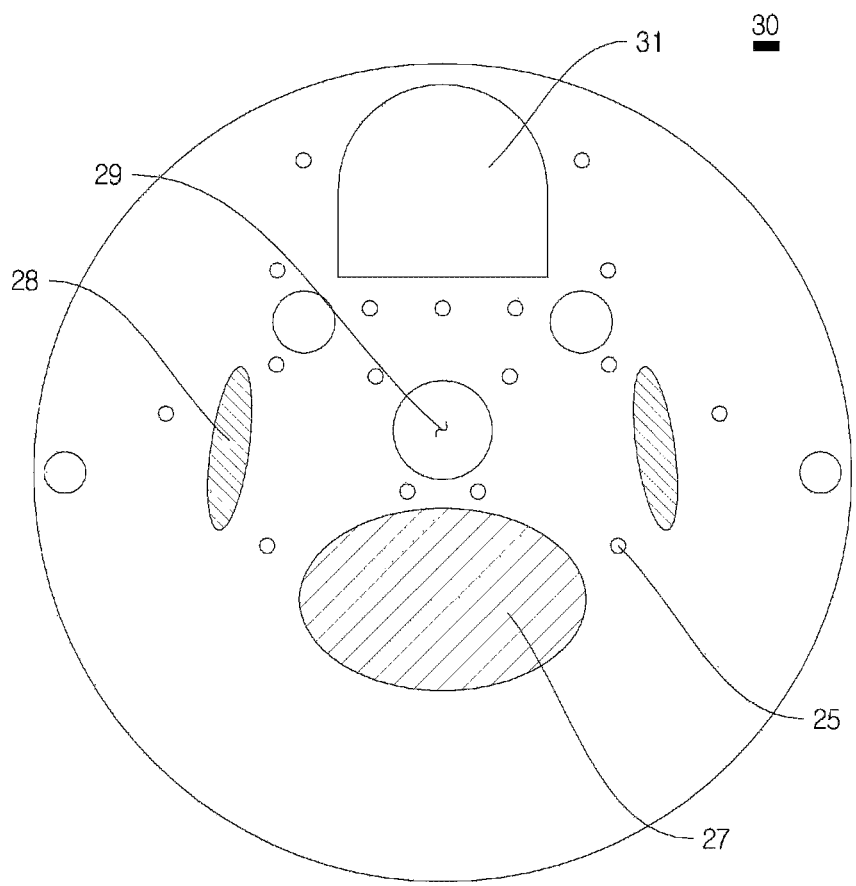
FIGS. 8 to 10 are schematic views showing the components of the head and neck simulation phantom device according to the second embodiment of the present invention.
Figure 9:
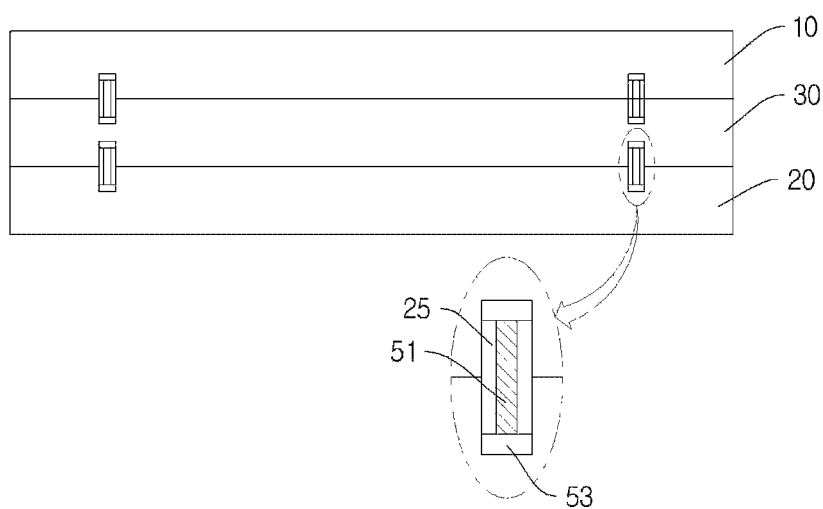
Figure 10:
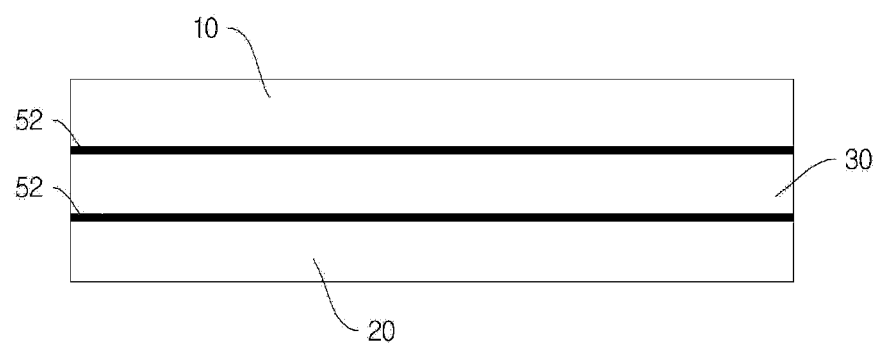

FIG. 1 is an exploded perspective view showing a head and neck simulation phantom device according to a first embodiment of the present invention, FIGS. 2 to 6 are schematic views showing the components of the head and neck simulation phantom device according to the first embodiment of the present invention, FIG. 7 is an exploded perspective view showing a head and neck simulation phantom device according to a second embodiment of the present invention, and FIGS. 8 to 10 are schematic views showing the components of the head and neck simulation phantom device according to the second embodiment of the present invention.

As shown in FIGS. 1 to 10, a first plate is denoted by a reference numeral 10, a first insertion groove by 11, a second plate by 20, a second insertion groove by 21, teeth simulants by 23, an accommodated material by 23a, a case by 23b, dosimeter insertion grooves by 25, cervical spine simulant by 27, mandible simulants by 28, through holes by 29, an intermediate plate by 30, an opening by 31, an auxiliary plate by 40, dosimeters by 51, films by 52, dosimeter fixtures by 53, couplers by 55 and fastening holes by 56.

A head and neck simulation phantom device according to a first embodiment of the present invention, which simulates the head and neck of a body, includes: the flat type first plate 10 having the first insertion groove 11 formed on one surface thereof; the flat type second plate 20 disposed to come into contact with the other surface of the first plate 10 and having the second insertion groove 21 formed on the contacted surface with the other surface of the first plate 10 in such a manner as to correspond to the first insertion groove 11; and the plurality of teeth simulants 23 inserted into the first insertion groove 11 and the second insertion groove 21 so as to simulate the teeth of the body, whereby the head and neck simulation phantom device can measure radiation, instead of the human body and can evaluate dose errors generated from teeth and implants within the body. According to the positions of a patient's cancer, in more detail, his or her mouth is fixedly closed or open, and in this state, he or she is subjected to radiation treatment. According to the first embodiment of the present invention, the head and neck simulation phantom device is adapted to simulate his or her head and neck in the state where his or her mouth is closed, so that artifacts expressed on CT images are obtained by using the first plate 10, the second plate 20 and the teeth simulants 23, and the dose on the corresponding region can be verified. On the other hand, an explanation on the head and neck simulation in the state where a patient's mouth is open will be given later.

The first plate 10 is a flat plate of a given thickness and has the first insertion groove 11 formed on one surface thereof. The first plate 10 is adapted to simulate the upper mouth structure of the body, and accordingly, the teeth simulants 23 adapted to simulate the upper teeth are insertedly coupled to the first insertion groove 11. The first plate 10 may have a circular section.

Figure 2:
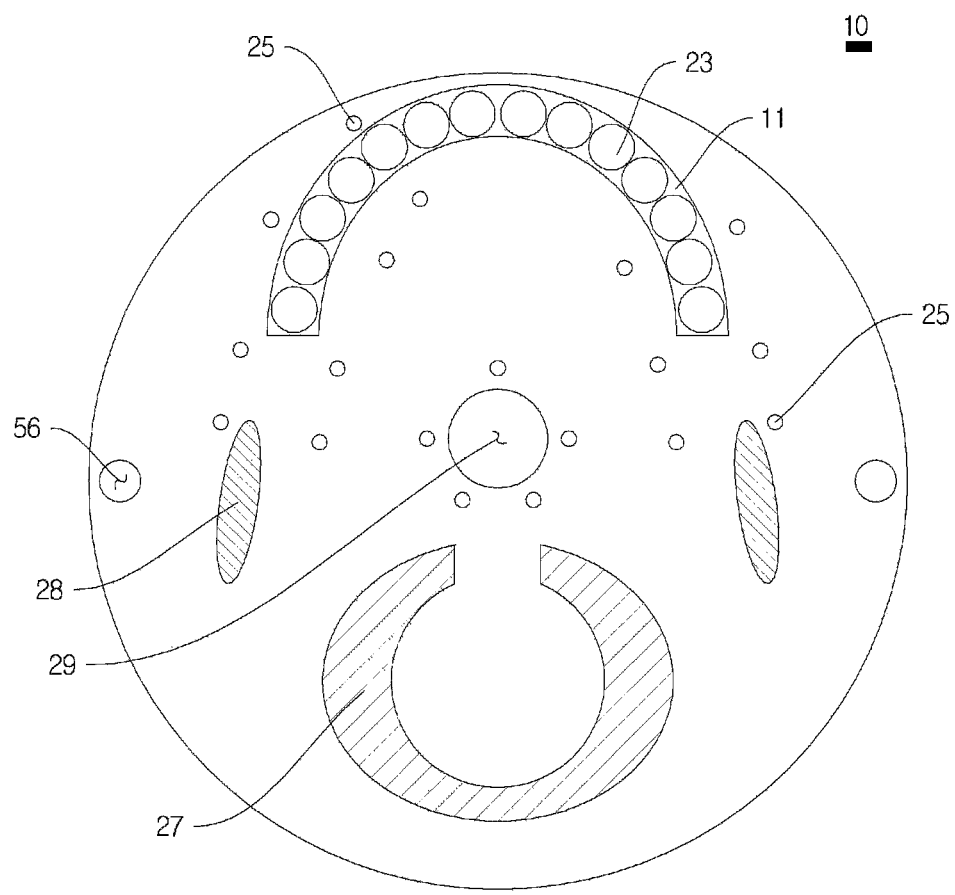
FIGS. 2 to 6 are schematic views showing the components of the head and neck simulation phantom device according to the first embodiment of the present invention.

FIG. 2 is a plan view showing the first plate 10, and as shown, the first plate 10 has the first insertion groove 11, the through hole 29, the cervical spine simulant 27, and the mandible simulants 28.

The first insertion groove 11 is the space into which the teeth simulants 23 are inserted. The first insertion groove 11 has a shape of an arch similar to the arrangement of the upper teeth of the body so that the curved surface of the arch is formed toward the outer periphery of the first plate 10 on one surface of the first plate 10.

The through hole 29 of a given area is formed on the center of the first plate 10, which simulates the nasopharynx of the body.

The cervical spine simulant 27 is formed at the opposite side to the first insertion groove 11 on one surface of the first plate 10 and made of a Teflon material similar to the material of the body bone, which simulates the cervical spine of the body. According to the present invention, the cervical spine simulant 27 is formed to a shape of C, but it may have various shapes, for example, a circle (See FIG. 3), an oval (See FIG. 8) and the like, according to the shapes of the patient's bone.

The mandible simulants 28 are adapted to simulate the mandible of the body and formed to the form of one pair in such a manner as to be adjacent to both end portions of the first insertion groove 11 on one surface of the first plate 10. The mandible simulants 28 have approximately oval shapes and are made of a Teflon material similar to the material of the body bone frame.

Like this, the upper mouth structure of the body is simulated with the first plate 10 and the first insertion groove 11, the through hole 29, the cervical spine simulant 27, and the mandible simulants 28 formed on the first plate 10.

The second plate 20 is disposed to come into contact with the other surface of the first plate 10 and has the second insertion groove 21 formed on the contacted surface with the other surface of the first plate 10 in such a manner as to correspond to the first insertion groove 11.

The second plate 20 is adapted to simulate the lower mouth structure of the body, and accordingly, the teeth simulants 23 adapted to simulate the lower teeth are insertedly coupled to the second insertion groove 21. The second plate 20 may have a circular section.

Figure 3:
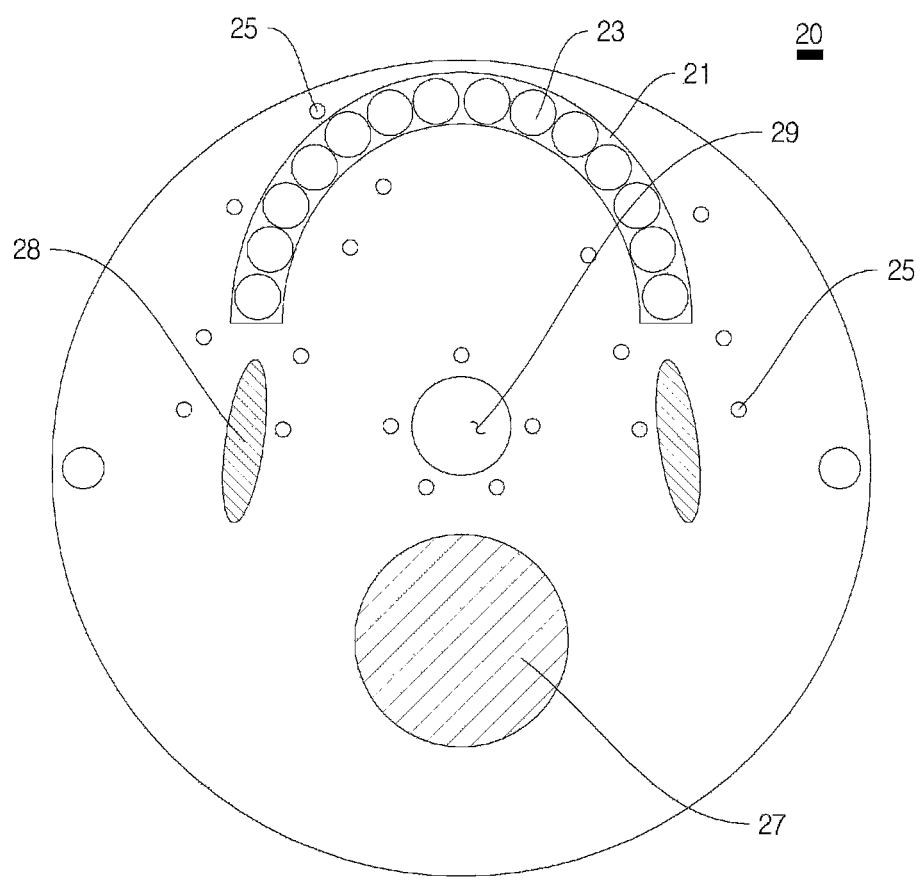

FIG. 3 is a plan view showing the second plate 20, and as shown, the second plate 20 has the second insertion groove 21, the through hole 29, the cervical spine simulant 27, and the mandible simulants 28.

The second insertion groove 21 is the space into which the teeth simulants 23 are inserted. The second insertion groove 21 has a shape of an arch similar to the arrangement of the lower teeth of the body so that the curved surface of the arch is formed toward the outer periphery of the second plate 20 on one surface of the second plate 20.

The through hole 29 of a given area is formed on the center of the second plate 20, which simulates the nasopharynx of the body. The through hole 29 formed on the second plate 20 communicates with the through hole 29 formed on the first plate 10.

The cervical spine simulant 27 is formed at the opposite side to the second insertion groove 21 on one surface of the second plate 20 and made of a Teflon material similar to the material of the body bone, which simulates the cervical spine of the body. According to the present invention, the cervical spine simulant 27 is formed to a shape of a circle, but it may have various shapes, like the cervical spine simulant 27 of the first plate 10.

The mandible simulants 28 are adapted to simulate the mandible of the body and formed to the form of one pair in such a manner as to be adjacent to both end portions of the second insertion groove 21 on one surface of the second plate 20. The mandible simulants 28 have approximately oval shapes and are made of a Teflon material similar to the material of the body bone frame.

Like this, the lower mouth structure of the body is simulated with the second plate 20 and the second insertion groove 21, the through hole 29, the cervical spine simulant 27, and the mandible simulants 28 formed on the second plate 20.

On the other hand, auxiliary plates 40 are coupled to top of the first plate 10 and underside of the second plate 20 so as to cover the first plate 10 and the second plate 20 (See FIG. 1). Accordingly, the first plate 10, the second plate 20 and the auxiliary plates 40 are laminated on each other to simulate the head and neck of the body. The auxiliary plates 40 have holes for simulating the nasal apertures and maxillar sinus of the body, and in some cases, the auxiliary plates 40 are laid on top of each other (See FIG. 1).

The plurality of teeth simulants 23 is inserted into the first insertion groove 11 and the second insertion groove 12, thereby simulating the teeth of the body. The teeth simulants 23 are continuously arranged in the first insertion groove 11 and the second insertion groove 12 or sparsely thereinto, thereby accurately simulating the teeth arrangement of the body.

Figure 4:
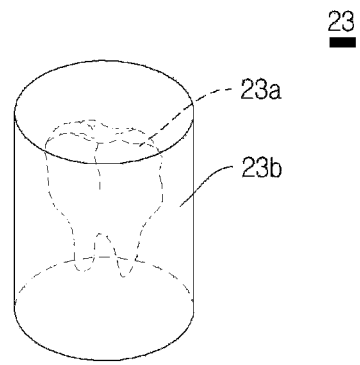

FIG. 4 is a schematic view showing each teeth simulant 23, and as shown, the teeth simulant 23 includes a cylindrical case 23b and an accommodated material 23a located in the case 23b.

The case 23b has a shape of a cylinder having a hollow portion formed at the inside thereof and may have a circular section. The case 23b is adapted to locate the accommodated material 23a therein and also inserted into the first insertion groove 11 and the second insertion groove 12 in such a manner as to be disposed continuously or sparsely with the adjacent case 23b.

Each accommodated material 23a is a tooth or implant taken from the body. The teeth simulants 23 simulate the teeth arrangement of the patient, and since the implants may be disposed between the teeth according to the teeth arrangement of the patient, the cases 23b with the teeth or implants are arranged in the first insertion groove 11 and the second insertion groove 12 in such a manner as to correspond to the teeth arrangement of the patient. The teeth or implants have different shapes from each other, and if only the teeth or implants are arranged therein, without having any cases 23b, there are gaps between the teeth or implants and the first insertion groove 11 and the second insertion groove 12, thereby giving bad influences on the measurement of dose. Accordingly, the teeth or implants are inserted into the uniformly shaped cases 23b, thereby minimizing the gaps and achieving accurate radiation measurement. Each case 23b is made of a thermoplastic, and as the thermoplastic is easily machined, the case 23b has the interior corresponding to the shape of the accommodated material 23a and the exterior having the uniform cylindrical shape. Further, the thermoplastic has equivalent properties to the tissues of the body, thereby allowing the radiation measurement to be accurately achieved.

On the other hand, the accommodated material 23a is made of titanium or high atomic number materials used as dental prosthesis. The titanium is used as a main material of the implant, thereby simulating the material of the implant in the mouth.

The cases 23b have serial numbers indicated thereon so as to identify the accommodated materials 23a located therein. The materials of the accommodated materials 23a located in the cases 23b are identified with the serial numbers indicated on the cases 23b by a surgeon, and after the accommodated materials 23a are appropriately selected, the cases 23b are inserted into the first insertion groove 11 and the second insertion groove 12.

Further, the teeth simulants 23, which are made of other materials, are selectively inserted into the first insertion groove 11 and the second insertion groove 12 by the surgeon, thereby applying the real state of the patient' teeth to the teeth simulants 23.

Through the first plate 10, the second plate 20 and the teeth simulants 23, like this, dose errors generated from the teeth and implants of the body can be evaluated, and the real state of the patient's teeth is applied, thereby accurately obtaining artifacts having various shapes and characteristics expressed on images by the teeth and implants.

FIG. 5 is a sectional view showing the insertion of dosimeters 51 in the state where the first plate 10 and the second plate 20 are laid on each other. As shown, the dosimeter insertion grooves 25 are formed along the outer edges of the first insertion groove 11 and the second insertion groove 21 in such a manner as to penetrate into the contacted surface between the first plate 10 and the second plate 20 (See FIGS. 2 and 3).

The dosimeters 51 are adapted to measure radiation dose, that is, dose absorbed according to the variations of energy levels of electrons through radiation. According to the present invention, the dosimeters 51 are thermo luminescence dosimeters or glass dosimeters. In case of the glass dosimeters, excited electrons are returned to specific energy levels, while being not dropped to ground state, so that even if errors occur in reading process, measured values can be read repeatedly.

The dosimeters 51 are insertedly disposed into the dosimeter insertion grooves 25 formed along the edges of the first insertion groove 11 of the first plate 10 and the second insertion groove 21 of the second plate 20, thereby verifying the accuracy of the dose expected at points where there is a high probability of the appearance of the artifacts, for example, around air cavities or implants having high atomic numbers. The dosimeters 51 are disposed around the cervical spine simulant 27, the mandible simulants 28 and the through hole 29, thereby evaluating the dose errors generated from the air or bone. The dosimeters 51 have shapes of cylinders corresponding to the shapes of the dosimeter insertion grooves 25.

Referring to FIG. 5, the dosimeter insertion grooves 25 are formed to penetrate into the contacted surface between the first plate 10 and the second plate 20, and the dosimeters 51 are inserted into the first plate 10 and the second plate 20 by half of the length. The shapes of the dosimeters 51 correspond to the shapes of the dosimeter insertion grooves 25 in such a manner as to be fixedly inserted into the dosimeter insertion grooves 25. Moreover, the dosimeters 51 are accurately fixed to the first plate 10 and the second plate 20 by means of dosimeter fixtures 53 disposed on both end portions thereof.

FIG. 6 is a sectional view showing the location of the film 52 between the first plate 10 and the second plate 20 in the state where the first plate 10 and the second plate 20 are laid on each other.

The film 52 is located between the first plate 10 and the second plate 20, thereby measuring the distribution of the radiation dose. The dosimeters 51 are adapted to measure one-dimensional point dose, and the film 52 is adapted to measure two-dimensional dose distribution. Through the two kinds of dose measurements, the radiation dose distribution can be accurately evaluated. If an air layer is formed between the film 52 and the first plate 10 and the second plate 20 upon the insertion of the film 52 between the first plate 10 and the second plate 20, dose measurement errors may be generated, and so as to prevent the air layer from being formed, accordingly, the film 52 comes into close contact with the first plate 10 and the second plate 20 by means of the couplers 55 as will be discussed later.

If the dose is measured by means of the film 52, air may enter the empty spaces of the dosimeter insertion grooves 25, thereby giving bad influences on the dose measurement. Accordingly, cylinders (not shown) made of acrylic and having the same sizes as the dosimeters 51 are first inserted into the dosimeter insertion grooves 25, and next, the dose measurement is conducted by means of the film 52.

On the other hand, the fastening holes 56 are formed penetratedly on the first plate 10 and the second plate 20, and next, the first plate 10 and the second plate 20 are coupled to each other by means of the couplers 55 inserted into the fastening holes 56. According to the first embodiment of the present invention, the couplers 55 include means for fastening and fixing objects, like bolts and nuts, rivets and so on. At this time, the couplers 55 are made of acrylic so that accurate radiation measurement can be achieved.

Referring to FIG. 7, on the other hand, an explanation on a head and neck simulation phantom device according to a second embodiment of the present invention will be in detail given. According to the second embodiment of the present invention, the head and neck simulation phantom device further includes at least one or more intermediate plates 30 disposed between the first plate 10 and the second plate 20 and having an opening 31 formed thereon in such a manner as to correspond to the first insertion groove 11 and the second insertion groove 21.

In the state where patients under the radiation treatment open their mouth according to their state, their CT images are photographed, and in this case, air cavity is formed in the mouth, thereby making it easy to produce artifacts around the air cavity and to cause many dose errors due to electronic jamming. According to the positions of the patient's cancer, in more detail, his or her mouth is fixedly open, and in this state, he or she is subjected to radiation treatment. In this case, the position of the tongue and the mouth are fixed by means of a tongue compressor and a mouth piece, and next, the CT images are obtained, thereby calculating the absorbed dose. According to the second embodiment of the present invention, the head and neck of the body can be simulated in the state where the patient's mouth is open by means of the intermediate plate 30.

The opening 31 of the intermediate plate 30 is adapted to simulate the air cavity in the mouth, and the at least one or more intermediate plates 30 are located between the first plate 10 and the second plate 20 to accurately provide the real structure of the patient's mouth when the CT images are photographed in the state where he or she opens the mouth and to accurately evaluate the dose errors.

FIG. 8 is a plan view showing the intermediate plate 30, and as shown, the configuration of the intermediate plate 20 is the same as those of the first plate 10 and the second plate 20 except that the opening 31 is formed correspondingly to the first insertion groove 11 and the second insertion groove 21. Accordingly, an explanation on the same components of the intermediate plate 30 as those of the first plate 10 and the second plate 20 will be avoided for the brevity of the description.

The opening 31 is formed penetratedly on the corresponding portion of the intermediate plate 30 to the first insertion groove 11 and the second insertion groove 21.

On the other hand, FIG. 9 is a sectional view showing the insertion of dosimeters 51 in the state where the intermediate plate 30 is disposed laminatedly between the first plate 10 and the second plate 20. As shown, the dosimeter insertion grooves 25 are formed along the outer edges of the first insertion groove 11 and the second insertion groove 21 on the first plate 10, the second plate 20 and the intermediate plate 30 in such a manner as to penetrate into the contacted surface between the first plate 10 and the intermediate plate 30 and the contacted surface between the second plate 20 and the intermediate plate 30.

The dosimeters 51 are inserted into the first plate 10 and the intermediate plate 30 by half of the length and into the second plate 20 and the intermediate plate 30 by half of the length.

FIG. 10 is a sectional view showing the location of the films 52 between the first plate 10 and the intermediate plate 30 and between the intermediate plate 30 and the second plate 20 in the state where the intermediate plate 30 is disposed laminatedly between the first plate 10 and the second plate 20. As shown, the films 52, which are disposed between the first plate 10 and the intermediate plate 30 and between the intermediate plate 30 and the second plate 20, are adapted to measure the radiation dose distribution.

The configuration as shown in FIGS. 9 and 10 is the same as that in which the first plate 10 and the second plate 20 are laid on each other except that the intermediate plate 30 is located between the first plate 10 and the second plate 20, and accordingly, an explanation on the same configuration and effects will be avoided for the brevity of the description. Further, FIGS. 9 and 10 show the single intermediate plate 30 disposed between the first plate 10 and the second plate 20, but of course, two or more intermediate plates 30 are disposed therebetween.

As described above, the head and neck simulation phantom device according to the present invention can measure radiation, instead of the human body, and evaluate dose errors generated from teeth and implants within the body.

Further, the head and neck simulation phantom device according to the present invention can selectively dispose teeth and implants to express the real state of the patient's teeth, so that artifacts appearing on the computed tomography CT images by the teeth and implants are obtained, thereby conducting dose verification on the corresponding regions of the CT images at which the artifacts appear.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above teachings. It is therefore intended that the scope of the invention be limited not by this detailed description, but rather by the claims appended hereto.

What is claimed is:

1. A head and neck simulation phantom device for simulating the head and neck of a body, the phantom device comprising:
   a flat type first plate having a first insertion groove formed on one surface thereof;
   a flat type second plate disposed to come into contact with the other surface of the first plate and having a second insertion groove formed on the contacted surface with the other surface of the first plate in such a manner as to correspond to the first insertion groove; and
   a plurality of teeth simulants inserted into the first insertion groove and the second insertion groove and for simulating the teeth of the body;
   wherein each teeth simulant comprises a cylindrical case and an accommodated material located in the case.

2. The head and neck simulation phantom device according to claim 1, wherein the first plate and the second plate have through holes formed penetratedly thereinto.

3. The head and neck simulation phantom device according to claim 1, wherein the accommodated material comprises a titatnium material or a tooth.

4. The head and neck simulation phantom device according to claim 1, wherein the case is made of a thermoplastic material.

5. The head and neck simulation phantom device according to claim 1, wherein the first plate and the second plate have a film therebetween so as to measure radiation dose distribution.

6. The head and neck simulation phantom device according to claim 1, further comprising couplers inserted penetratedly into fastening holes formed penetratedly into the first plate and the second plate so as to couple the first plate and the second plate to each other.

7. The head and neck simulation phantom device according to claim 1, further comprising at least one or more intermediate plates disposed between the first plate and the second plate and having an opening formed thereon in such a manner as to correspond to the first insertion groove and the second insertion groove.

8. The head and neck simulation phantom device according to claim 7, wherein the first plate, the second plate and the intermediate plate have dosimeter insertion grooves formed along the outer edges of the first insertion groove and the second insertion groove in such a manner as to penetrate into the contacted surface between the first plate and the intermediate plate and the contacted surface between the second plate and the intermediate plate and to insert dosimeters for radiation measurement thereinto.

9. The head and neck simulation phantom device according to claim 8, wherein the dosimeters are inserted into the first plate and the intermediate plate by half of the length and into the second plate and the intermediate plate by half of the length.

10. The head and neck simulation phantom device according to claim 7, wherein the first plate and the intermediate plate have a film disposed therebetween and the intermediate plate and the second plate have a film disposed therebetween, so as to measure radiation dose distribution.

11. A head and neck simulation phantom device for simulating the head and neck of a body, the phantom device comprising:
   a flat type first plate having a first insertion groove formed on one surface thereof;
   a flat type second plate disposed to come into contact with the other surface of the first plate and having a second insertion groove formed on the contacted surface with the other surface of the first plate in such a manner as to correspond to the first insertion groove; and
   a plurality of teeth simulants inserted into the first insertion groove and the second insertion groove and for simulating the teeth of the body;
   wherein the first plate and the second plate have dosimeter insertion grooves formed along the outer edges of the first insertion groove and the second insertion groove in such a manner as to penetrate into the contacted surface therebetween and to insert dosimeters for radiation measurement thereinto.

12. The head and neck simulation phantom device according to claim 11, wherein the dosimeters are inserted into the first plate and the second plate by half of the length.

* * * * *